United States Patent [19]

Boiarski et al.

[11] Patent Number: 4,727,730

[45] Date of Patent: Mar. 1, 1988

[54] INTEGRATED OPTIC SYSTEM FOR MONITORING BLOOD PRESSURE

[75] Inventors: Anthony A. Boiarski, Columbus; Nile F. Hartman, Westerville, both of Ohio; Rand C. Sherman, Holmdel, N.J.

[73] Assignee: Medex, Inc., Hilliard, Ohio

[21] Appl. No.: 884,219

[22] Filed: Jul. 10, 1986

[51] Int. Cl.[4] .............................................. A61B 5/02
[52] U.S. Cl. ..................................... 128/667; 128/675; 128/748; 73/705
[58] Field of Search ............................. 128/672–675, 128/748, 665–667, 633–634; 73/705, 708, 715

[56] References Cited

U.S. PATENT DOCUMENTS

| 3,249,105 | 5/1966 | Polanyi . | |
| 3,267,932 | 8/1966 | Valliere . | |
| 3,273,447 | 9/1966 | Frank . | |
| 3,814,081 | 6/1974 | Mori . | |
| 3,822,695 | 7/1974 | Takayama . | |
| 4,030,485 | 6/1977 | Warner . | |
| 4,078,432 | 3/1978 | Stewart | 73/705 |
| 4,158,310 | 6/1979 | Ho | 73/705 |
| 4,194,217 | 3/1980 | Van Den Bosch | 128/633 X |
| 4,201,222 | 5/1980 | Haase | 128/673 X |
| 4,210,029 | 7/1980 | Porter | 128/748 X |
| 4,368,645 | 1/1983 | Glenn et al. | 73/705 |
| 4,487,206 | 12/1984 | Aagard | 128/672 |
| 4,543,961 | 10/1985 | Brown | 128/675 X |
| 4,560,248 | 12/1985 | Cramp et al. | 128/634 X |
| 4,593,701 | 6/1986 | Kobayashi et al. | 128/667 |
| 4,611,600 | 9/1986 | Cohen | 128/667 |
| 4,626,680 | 12/1986 | Martens et al. | 73/705 X |

FOREIGN PATENT DOCUMENTS 0063778 11/1982 European Pat. Off. ............. 128/748

Primary Examiner—Edward M. Gorer
Assistant Examiner—Angela D. Sykes
Attorney, Agent, or Firm—Wood, Herron & Evans

[57] ABSTRACT

Blood gases and the like are monitored by a single probe having multiple dye wells and dyes immobilized in the wells, the dyes being exposed to the blood gases. Optical fibers and waveguides connected to the dye wells permit light to be directed from a light source to the dyes and the light due to absorption or the spontaneous emission of the dye returned to a light detector. The intensity, phase shift or other mechanism of the returned radiation is a measure of the partial pressure of a respective blood gas.

3 Claims, 7 Drawing Figures

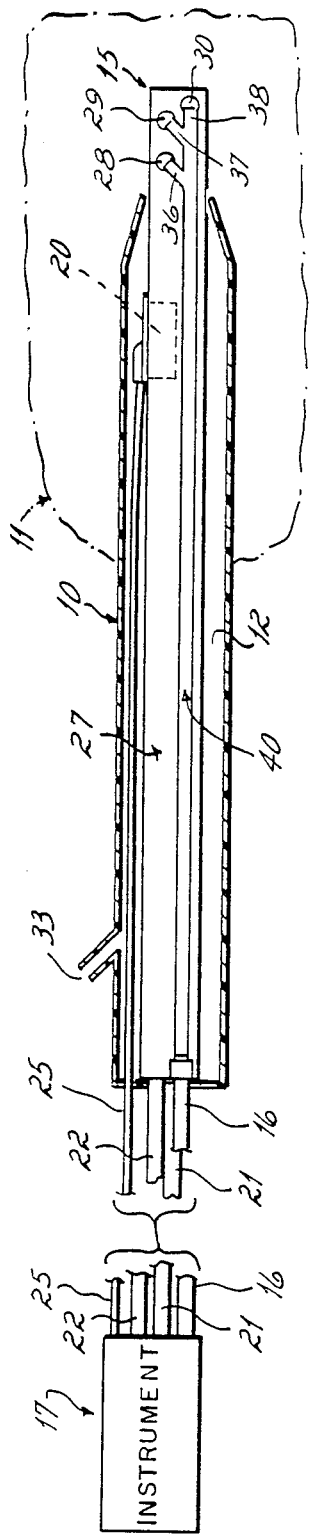
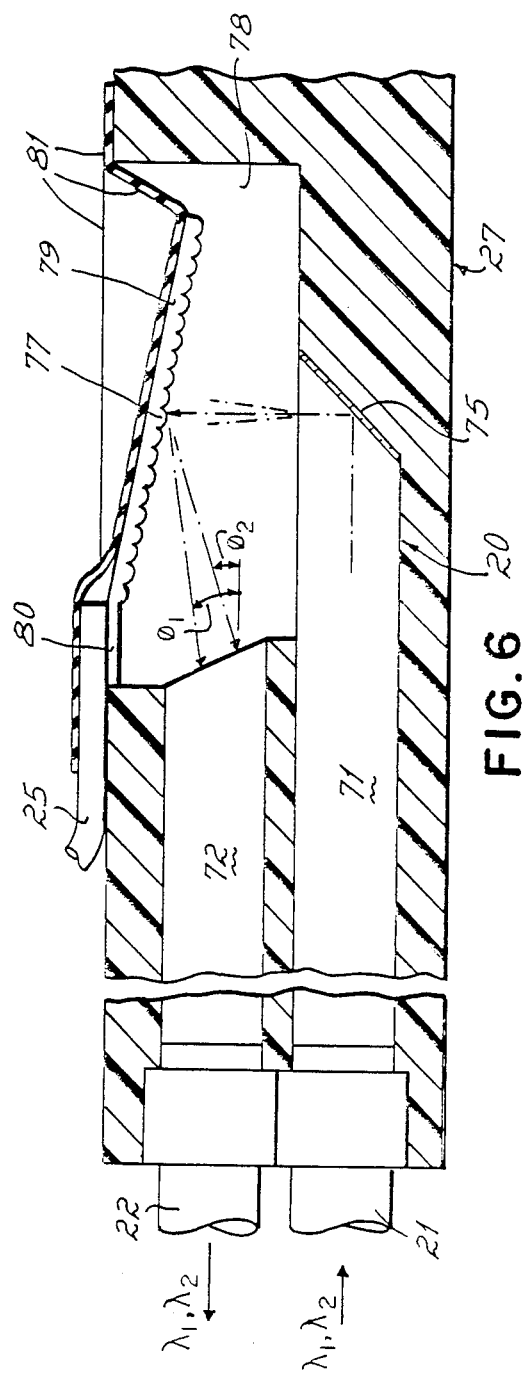

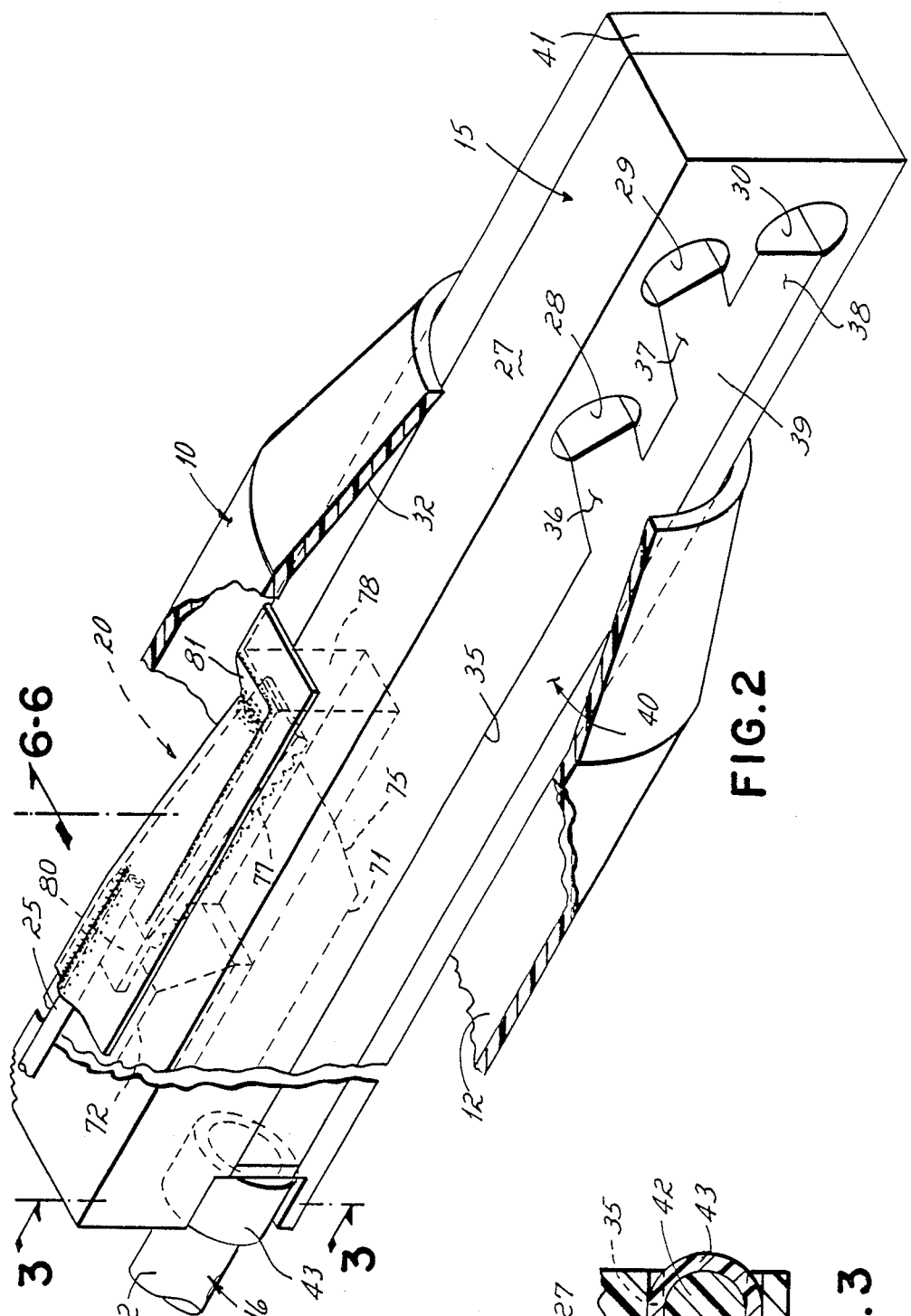

INTEGRATED OPTIC SYSTEM FOR MONITORING BLOOD PRESSURE

BACKGROUND OF THE INVENTION

This invention relates to a probe for monitoring constituents in a bodily fluid such as blood, and more particularly, the invention relates to a probe as part of an apparatus for continuously monitoring the constituents in the blood including, pH, $pCO_2$ and $pO_2$, blood electrolytes and blood pressure.

Over the years, considerable research and development work has been carried on in the field of monitoring gases but not necessarily restricted to blood gases. Within the last twenty years or so, attention has been given to the development of monitoring systems having the following components: a dye to react with the constituents being monitored, a structure for holding the dye, a membrane separating the monitored analyte from the dye, and a system for directing light onto the dye and monitoring the returned radiation, the intensity of the return radiation being a measure of the constituent passing through the membrane and contacting the dye.

Two primary systems have been proposed. In the first, a system for measuring $O_2$, for example, a fluorescent dye is excited by the incoming light source to cause it to fluoresce. The wavelength of fluorescence is different from the wavelength of the incoming light source. Oxygen will tend to quench the intensity of fluorescence. The degree of quenching becomes a measure of the pressure of oxygen in the fluid being monitored.

Another known system employs an absorption based dye. The dye is irradiated by light of known intensity. The absorption capability of the dye is affected by the constituent whose presence is being monitored. The intensity of the incoming light is compared to the intensity of the light scattered back from the dye to determine the quantity of the constituent in the blood.

At the present time, there has been no production of a single probe which is small enough (less than a millimeter in dimension) to be inserted into a blood vessel for the continuous monitoring of the triad of pH, $CO_2$ and $O_2$. The problem appears to be that there has been no practical design for and method of manufacturing such a tiny device which satisfies all the criteria for a commercially successful device such as low cost for disposability, absence of toxicity, capability of being sterilized and the like.

SUMMARY OF THE INVENTION

It has been an objective of the present invention to provide a tiny probe having a maximum transverse dimension of about 0.625 mm and thus being capable of being passed through a 20 gauge catheter cannula whose minimum internal diameter is 0.711 mm. The probe is connected by optical fibers to monitoring apparatus and is capable of providing real time information concerning one or more constituents of blood.

It has been another objective of the invention to provide a probe for the measurement of blood pressure and mounted on the same probe as that which measures partial pressures or constituents of blood.

It has been another objective of the invention to provide a probe which is capable of holding a dye, the dye being accessible through a permeable substance, and the probe having an optical system capable of interrogating the dye.

It has been another objective of the invention to provide a method of manufacturing an integrated optic probe of the type described herein.

These objectives are attained by providing a plastic base, forming one or more dye wells in the plastic base, forming, in the plastic base, waveguides that provide light paths to the dye wells and mounting optical fibers onto the base in optical communication with the waveguides so as to bring incoming light to the dye wells and to return the radiation from the dye wells to monitoring apparatus.

The base is formed by a photofabrication process which includes the steps of forming a block of light-hardenable material, masking the portion of that material to be removed and subjecting the remainder to light to harden it. Thereafter, the masked portion is washed away, leaving one or more dye wells, as desired, and channels in the block connected to the dye wells, the channels to be subsequently formed as waveguides. A deposit of optical cement in the channel followed by the optical hardening of it creates the waveguides to the respective dye wells.

In a preferred form of the invention, a single optical fiber is cemented in the block and is connected by a main waveguide and branch waveguides to the dye wells. The dyes selected are fluorescing type dyes and are immobilized in substances that are selectively permeable to the gases under observation. A source, capable of producing multiple differing wavelengths is directed through a multiplexer to the single optical fiber to excite the dyes. The wavelengths emanating from the fluorescing dye are returned and their intensities measured to provide a measurement of the constituents being observed.

For the measurement of blood pressure, the invention provides a block having a cavity therein. The cavity is covered by a cantilevered diffraction grating and a flexible seal which flexes in response to changes in blood pressure and thereby causes the diffraction grating to pivot. Optical fibers and waveguides direct light of two wavelengths onto the diffraction grating and direct the reflected light back to measuring apparatus. A ratio of the intensity of the reflected beams provides a measure of the deflection of the gratings and hence blood pressure. Intensity is not the only method of determining analyte concentration. Lifetime decay (phase shift) plus others can be used.

Another feature of the invention resides in the mounting of the blood pressure monitoring probe on the blood gas monitoring probe. The mounting is such that, when passed through a cannula, the dye wells on the blood gas probe will be positioned beyond the cannula and the blood pressure probe will remain within the cannula. A heparin solution, which is slowly introduced into the blood stream through the cannula, provides the communication of the pressure of the blood to the probe within the cannula.

BRIEF DESCRIPTION OF THE DRAWINGS

The several features and objectives of the invention will become more readily apparent from the following detailed description taken in conjunction with the accompanying drawings in which:

FIG. 1 is a diagrammatic elevational view illustrating the invention.

FIG. 2 is a perspective view of the probe and cannula combination.

FIG. 3 is a cross sectional view taken along lines 3—3 of FIG. 2.

FIG. 6 is a diagrammatic cross sectional view of a blood pressure monitoring probe.

DESCRIPTION OF THE PREFERRED EMBODIMENTS

General Organization and Operation

Figure 4:
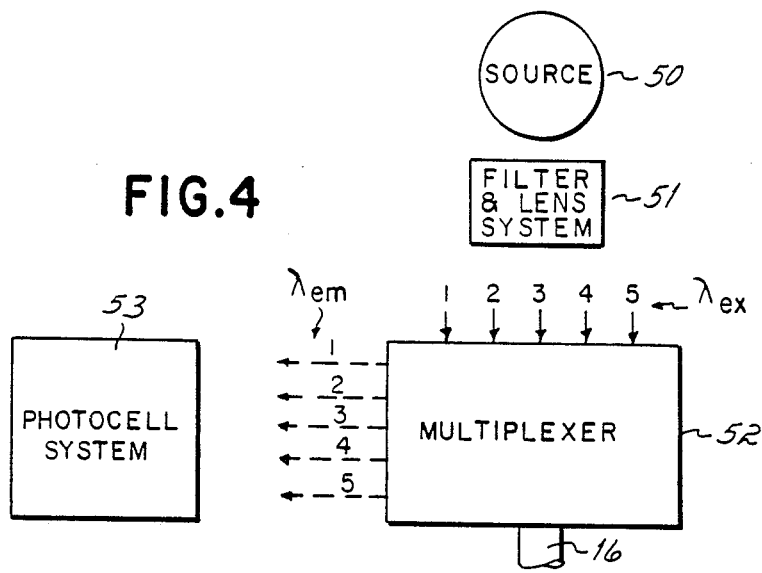
FIG. 4 is a diagrammatic view of a portion of the monitoring apparatus.

As shown in FIG. 1, a cannula 10 is inserted into the blood vessel of a patient indicated at 11. The cannula has an internal bore 12. Passing through the bore and partially projecting slightly beyond the cannula is a probe 15 which is connected by at least one optical fiber 16 to an instrument 17 whose functions will be described.

Mounted on the probe 15 is a blood pressure probe 20, and two optical fibers 21 and 22 connected to the instrument 17. Further, a tube 25 is connected to the blood pressure probe to introduce a reference pressure into the probe, as will be described below.

As best shown in FIG. 2, the blood gas probe consists of a block 27 in which three dye wells 28, 29 and 30 are formed. The block 27 is tiny, having a maximum dimension across the diagonal, in cross section, of about 0.625 mm. Its thickness is about 0.38 mm. and its width is about 0.5 mm. These dimensions permit the probe to pass through the cannula bore 12 which is about 0.90 mm. in diameter. The tip of the bore where it is tapered inwardly, as shown at 32, has a maximum diameter of about 0.711 mm. It is necessary to provide spacing between the inside diameter of the cannula tip and the outside dimensions of the probe to permit the flow of a heparin solution from an injection site 33 (FIG. 1) to the bloodstream in the artery to prevent clotting of the blood. Additionally, it may be necessary from time to time to take blood samples through the injection site 33.

Each dye well forms a sensor for a specific blood gas. Let it be assumed that dye well 28 is for sensing oxygen $O_2$, dye well 29 is for $CO_2$ and dye well 30 is for pH. Each dye well contains a dye which is excited to fluorescence by an incoming beam of a preselected wavelength. The intensity of the fluorescence is measured. That fluorescence is to be selectively quenched by the particular blood gas associated with the dye.

The dye well can be covered by a membrane selectively permeable for the blood gas to be measured or, alternatively and preferably, the dye can be immobilized in a porous matrix which is selectively permeable to the gas being measured. For example, the $O_2$ and $CO_2$ can be disposed in a matrix of silicone rubber. The dye for the $O_2$ is insensitive to $CO_2$. The dye for the $CO_2$ is insensitive to $O_2$. The silicone rubber is hydrophobic and will block permeation of water and the larger gas molecules.

The dye well 30 contains a fluorescing dye embedded in a porous matrix of acrylamide gel which is hydrophilic and thus permits the passage of water containing the H ion. The dye contained within the matrix is sensitive only to the hydrogen ion.

An optical channel 35 having branches 36, 37 and 38 is connected to each dye well. The channel is filled with an optical cement 39 which is hardened and which, in combination with the block which forms the channel, creates a waveguide 40 leading to each dye well. The optical fiber 16 is connected in the channel 35 in abutment with the waveguide to form a substantially loss-free optical path from the apparatus 17 to the waveguide and back.

To facilitate the understanding of the operation of the blood gas monitor, a fairly basic system will be first described.

A light source within the apparatus 17 will be directed through the optical fiber and waveguide 35 to each dye well to excite the dye contained within the dye well to fluoresce. Each dye will fluoresce at its own frequency or wavelength. The intensity of the unquenched fluorescence is known. When each dye is subjected to the respective blood gas to which it is sensitive, its intensity of fluorescence will be quenched. The degree of quenching will be the measure of the partial pressure of the blood gas under observation. The foregoing system is an over simplification of the operation of the monitoring apparatus. A more specific description of the probe and its operation to measure blood gases will be set forth hereinafter.

THE PROBE

The configuration of the probe is dictated to some extent by the size of the cannula through which it is passed. The cannula shown in FIG. 2 is about 50 mm. long and has an inside diameter of about 0.90 mm. The tip 32 is tapered and has a minimum inside diameter of 0.711 mm.

The overall dimensions of the probe are therefore preferred to be 0.38 mm. thick and 0.5 mm. wide. The length of the probe is slightly greater than 50 mm. so that the probe fills the flexible 50 mm. portion of the cannula with the three dye wells projecting beyond the tip of the cannula as shown in FIG. 2. Thus, the dye wells will be exposed to the comparatively rapid flow of blood (approximately 100 cc. per minute) as contrasted to the very slow flowing heparin solution of a few drops per minute passing through the cannula. The blood pressure probe 20, however, is preferably disposed within the cannula bore as shown. Since the pressure of the heparin solution within the cannula will be the same as the blood pressure, the blood pressure probe on the outside of the cannula does not have to be subjected directly to the blood.

Except for the base 41 which is an aluminum substrate, the block 27 is substantially entirely formed of a photopolymer film resist, that is, a monomer which is polymerized by ultraviolet light such as Riston manufactured by duPont. It will be flexible enough to bend with any flexure of the cannula in the artery.

Each block is formed with a channel configuration, as shown at 35-38. Each channel and branch is converted to a waveguide by filling with a photo-resist or optical cement such as Norland Optical Adhesive manufactured by Norland Products, Inc. of New Brunswick, N.J. The channel is of square cross section having a cross-sectional dimension of 0.112 mm. by 0.112 mm. A single optical fiber having a core diameter of 0.112 mm. is positioned in the channel 35 and is in abutment with the waveguide formed by the polymerized Norland material. The positioning of the optical fiber should be such that its core 42 lies exactly within the confines of the square waveguide material as shown in FIG. 3 with the cladding 43 projecting beyond the waveguide.

With this configuration, all of the excitation light will pass from the core into the waveguide without loss. The return light, emitted from the fluorescing dye, will substantially entirely all return to the core except for a small loss from the light at the corners of the waveguide which do not lie in abutment with the fiber core.

The optoelectronic system for interrogating the probe is diagrammatically illustrated in FIG. 4. As shown there, a source 50 directs light through a filter and lens system 51 to create five excitation wavelengths $\lambda ex$ 1–5. A multiplexer 52 transmits those excitation waves to the optical fiber 16 which in turn directs the waves to the dye wells. Excitation waves 1 and 2 interact with the dye in dye well 30 which monitors pH. Waves 3 and 4 interact with the dye and dye well 29 which measures $CO_2$. Wave 5 interacts with the dye well 28 which measures the oxygen $O_2$.

Each excitation wave creates a corresponding fluorescent wave which is transmitted through the waveguide 35 and the optical fiber back to the multiplexer as emitted wavelengths $\lambda em$ 1–5. These wavelengths are received by a photocell system 53 which measures their intensities.

The measurement systems for pH, $O_2$ and $CO_2$ are similar. A single source is filtered to provide excitation wavelengths. A multiplexer will sequence those wavelengths to excite the dye at different intervals of time. The fluorescence will be at a third wavelength. The intensity of the fluorescence created by the first wavelength will be different from the intensity of the fluorescence when excited by the second wavelength. The intensity of the fluorescing wavelength produced by each excitation wavelength will change with changes in concentration of $CO_2$ or pH. However, the intensity produced by one excitation wavelength will change at a rate different from the intensity produced by the other excitation wavelength. The ratio of those two intensities, assuming no variation in the intensity of the source, will be a measure of the pH and will remain constant regardless of losses occurring in the system. It is contemplated that the ratios of emitted intensities will be measured to determine pH and $CO_2$, $CO_2$ being essentially a pH measurement as is well known in the art.

The measurement of oxygen partial pressure cannot be done in that fashion. Instead, the oxygen-sensitive dye is excited by a single wavelength and the rate of decay of the emitted wave is measured. As a preliminary, it will have been determined, for the specific dye and excitation wavelength, what the rate of decay will be for different oxygen pressures. For example, if the pressure of oxygen is high, the rate of decay will be faster than if the pressure of oxygen is low. Thus, the instrument can be programmed to measure the length of time for the intensity of the emitted fluorescence to drop a preselected number of units of intensity. The time for decay, for one level of oxygen pressure, from one specified point to a lower specified point will always be the same regardless of losses in the system. Thus, when the decay times are known for the various levels of oxygen pressure, determining the decay time for an unknown blood will produce the desired information.

All of this apparatus is housed in a microprocessor-based instrument 17 that provides the necessary calculations and presents real time readouts of pH, $pO_2$, $pCO_2$ and blood pressure, as will be described hereinafter.

THE PROCESS OF MANUFACTURE OF THE GAS PRESSURE PROBE

One of the advantages of the present invention is the low cost for producing probes. The low cost is obtained through the integrated optic design of the probe which admits of mass production techniques as disclosed hereinafter.

Figure 5:
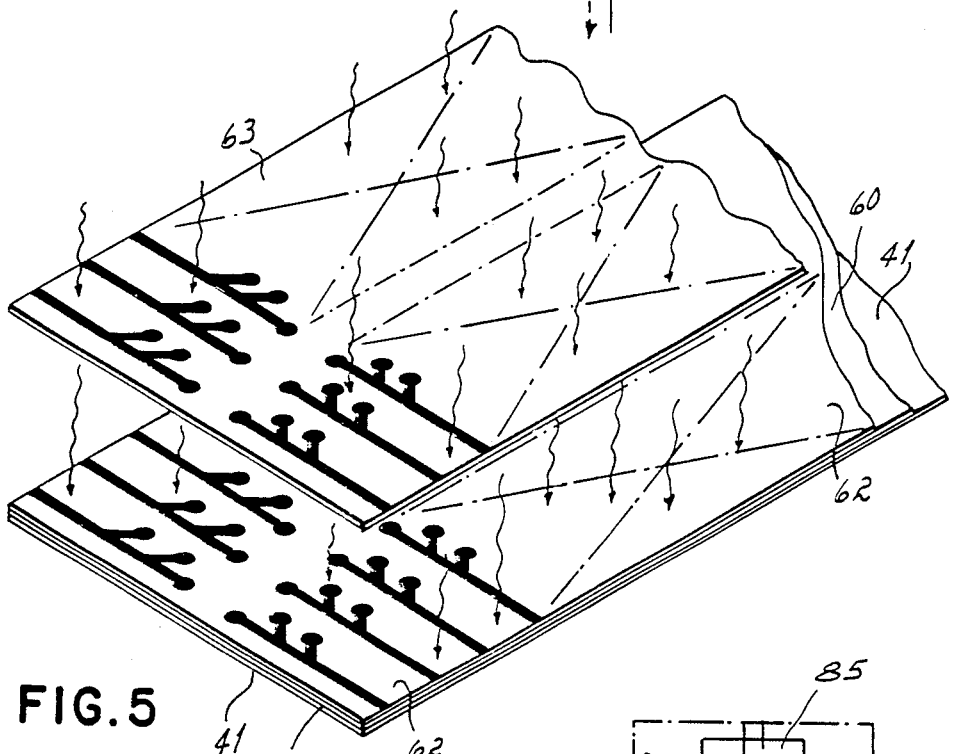
FIG. 5 is a diagrammatic view of the elements illustrating the process of manufacturing probes.

As shown in FIGS. 5, in the simultaneous manufacture of multiple probes a Riston layer 60 is mounted on an aluminum substrate 41. The Riston layer is subjected to ultraviolet light to harden it. These layers are in plan 100 mm by 200 mm and thus capable of making 800 probes having dimensions of $50 \times 0.5$ mm.

A second Riston layer 62 is applied to the Riston layer 60. It is 0.112 mm. thick which is the desired depth of each dye well and associated waveguide.

A mask 63 is applied to the Riston layer 62, the mask defining the dye wells 28, 29 and 30 and channels 35–38 to be formed for each probe. Since each probe is approximately one-half mm. wide, approximately 400 elements can be masked on one-half the strip and 400 elements masked on the other half of the strip. The thus masked strip is subjected to ultraviolet light to polymerize all unmasked portions of the strip. After exposure and hardening, the unhardened monomer is washed out with a solution with 1,1,1-trichlorethane leaving the dye wells and channels.

A photo-resist optical cement (Norland) is inserted in the dye wells and associated channels just formed.

A second mask is placed over the strip to mask each of the three dye wells and the length of channel 35 leading to the channel branches 36–38. With the strip thus masked, it is subjected to ultraviolet light. Again, the uncured optical cement is rinsed away. The cured or hardened cement forms the waveguide 40 leading from the optical fiber (to be inserted later) to the dye well. The strip is now ready for the introduction of the dyes. One system for introducing the dye and matrix, that is the gas permeable immobilizing material, into the wells consists simply of masking the entire surface of the strip except for the selected dye well (pH, for example). The dye and matrix is then spread over the surface so that it will get good penetration into each well. The excess is wiped off.

The matrix is cured in situ. This may be done by subjecting it to ultraviolet light where the matrix is a substance which can be cured by ultraviolet light. Alternatively, a hardener can be injected by a stepping apparatus of known design.

These sequences of operation are repeated until all three dye wells are filled and the matrices are cured.

Alternatively, the dye wells can be filled with the dye and an immobilizer and thereafter covered with a membrane selectively penetrable by the gas to be measured.

Having completed the insertion of the dye, the strip is then sawed into individual probes. Automatic handling equipment can be provided to deliver probes one at a time to an operator station where the operator places an optical fiber 16 in the available channel and secures with optical cement. The optical cement is thereafter cured by ultraviolet light to complete the formation of the probe.

An example of set of dyes and immobilizing matrix is as follows:

| Dye Well | Blood Gas | Dye | Immobilizer Matrix | Excitation Waves |
|---|---|---|---|---|
| 28 | $O_2$ | fluoranthene or coramene | silicone rubber | $\lambda 5$ |
| 29 | $CO_2$(HOPSA) | 8-hydroxy-1,3,6-pyrene tri sulfonic acid | silicone rubber | $\lambda 3$ $\lambda 4$ |
| 30 | pH(HOPSA) | 8-hydroxy-1,3,6-pyrene tri sulfonic acid | Acrylamide gel | $\lambda 1$ $\lambda 2$ |

In the foregoing description of the blood gas probe, there has been disclosed a single fiber probe that interrogates three dye wells each using a fluorescing dye. It should be understood that the invention is equally applicable to systems employing multiple fibers for communicating with respective dye wells such as electrolytes, that the invention is applicable to systems for measuring other blood constituents, and the invention is applicable to systems wherein absorption based dyes are employed to measure the analytes of interest.

BLOOD PRESSURE MONITOR

The blood pressure monitor is shown in FIG. 6.

The blood pressure probe includes the block 27. Preferably, the block is mounted on the blood gas probe, but it can be a separate unit. The block 27 contains waveguides 71 for two incoming beams and waveguide 72 for two outgoing beams. Each waveguide is connected to a respective optical fiber 21, 22. Wave guide 71 is terminated in a 45° mirror surface 75. An optical diffraction grating 77 is mounted above the mirror surface 75 in a cavity 78. The grating is mounted on a beam 79 which is cantilevered from a position 80 on the block 70. A flexible seal 81 overlies the grating and seals the cavity 78. A source of reference pressure, from tube 25, is connected to the cavity 78 to maintain the cavity at the desired reference pressure such as atmospheric pressure.

The pressure of the blood acts against the flexible seal 81 and causes the grating to flex inwardly. The angular displacement of the grating, flexing inwardly, is a measure of the blood pressure applied to the flexible seal.

Figure 7:
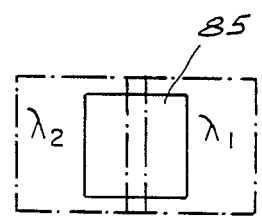
FIG. 7 is a diagrammatic view of the face of a waveguide onto which the light from the diffraction grating is reflected.

In the operation of the blood pressure probe, two beams of wavelength $\lambda 1$ and $\lambda 2$ are directed through the waveguide 71. Those two beams impinge upon the grating 77. Because of their different wavelengths, the beams will exit from the diffraction grating at differing angles $\phi 1$ and $\phi 2$ for $\lambda 1$ and $\lambda 2$, respectively. As shown in FIG. 7, 85 represents the face of the waveguide 72 upon which the beams impinge and are reflected off the grating. Depending upon the amount of angular shift imparted to the respective beams by the grating, which is in turn dependent upon their wavelengths, the beams will cover greater or lesser portions of the face of the waveguide 72. Thus, varied respective intensities of the beams are transmitted to the instrument 17 (FIG. 1) which provides a measure of the intensity of the beam of wavelength $\lambda 1$ and compares it to the intensity of the beam of wavelength $\lambda 2$. The ratio of the intensity of $\lambda 1$ as compared to $\lambda 2$ will be a measure of the amount of deflection of the grating 77 and, hence, blood pressure.

Each probe would be calibrated with a calibration number, or an identifying electronic tag, attached to it and as it was applied to the monitor. A gain adjustment in the monitor would have to be made to accommodate variations in the calibration of the probes one to the other.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

Having described our invention, we claim:

1. Blood pressure monitoring apparatus comprising, a block,
means defining a cavity in said block,
said cavity having an opening,
a resilient diaphragm overlying said opening and having an outside surface exposed to blood in a blood vessel,
a diffraction grating cantilevered over said opening and engaged by said diaphragm to bend said grating into said cavity upon application of blood pressure on the outside surface of said diaphragm,
means for directing a beam of light consisting of two wavelengths onto said diffraction grating,
light-receiving means presenting a surface in said cavity,
and means for measuring the quantity of each said wavelength impinging on said surface.

2. Blood pressure monitoring apparatus as in claim 1 further comprising,
parallel incoming and outgoing waveguides having ends extending into said cavity,
means guiding incoming beams from said incoming waveguide to said diffraction grating and onto said outgoing waveguide,
and optical fibers mounted between said waveguides and said measuring means.

3. Blood pressure monitoring apparatus comprising, a block having a cavity therein, a light source, first optical fibers connected between said light source and said cavity to direct light rays into said cavity,
a diffraction grating overlying said cavity and being in the path of said light rays, said diffraction grating deflecting in response to variations in fluid pressure external to said block,
monitoring means,
second optical fibers connected between said cavity and said monitoring means and positioned to receive reflections from said diffraction grating,
said monitoring means indicating variations in blood pressure dependent upon the amount of deflection of said diffraction grating.

* * * * *